(12) United States Patent
Minick

(10) Patent No.: US 7,666,823 B2
(45) Date of Patent: Feb. 23, 2010

(54) LENS CARE SOLUTIONS

(75) Inventor: Kasey Jon Minick, Cumming, GA (US)

(73) Assignee: Novartis AG, Basel (CH)

( * ) Notice: Subject to any disclaimer, the term of this patent is extended or adjusted under 35 U.S.C. 154(b) by 228 days.

(21) Appl. No.: 11/599,971

(22) Filed: Nov. 15, 2006

(65) Prior Publication Data

US 2007/0149426 A1 Jun. 28, 2007

Related U.S. Application Data

(60) Provisional application No. 60/737,206, filed on Nov. 16, 2005.

(51) Int. Cl.
*C11D 1/66* (2006.01)
*C11D 3/22* (2006.01)
*C11D 3/28* (2006.01)
*C11D 3/30* (2006.01)
*C11D 3/43* (2006.01)

(52) U.S. Cl. .................. 510/112; 510/383; 510/470; 510/477; 510/488; 510/500; 510/505; 510/506; 510/499

(58) Field of Classification Search .......... 510/112, 510/470, 383, 505, 506
See application file for complete search history.

(56) References Cited

U.S. PATENT DOCUMENTS 6,093,686 A * 7/2000 Nakada et al. ............. 510/112
6,790,409 B1 * 9/2004 Nakamura et al. ......... 422/22
2004/0142829 A1 * 7/2004 Tsao et al. ................. 510/112

FOREIGN PATENT DOCUMENTS

| WO | WO 02/55118 A1 | 1/2002 |
| WO | WO 02/062260 A2 | 8/2002 |
| WO | WO 2004/024855 | 3/2004 |
| WO | WO 2004/054629 | 7/2004 |

OTHER PUBLICATIONS

International Search Report and Written Opinion, (Feb. 2007).

* cited by examiner

*Primary Examiner*—Gregory R Del Cotto
(74) *Attorney, Agent, or Firm*—Sheng-Hsin Hu; Jian Zhou

(57) ABSTRACT

The present invention provides solutions containing dexpanthenol in combination with xylitol, preferably further including a viscosity-enhancing agent to make solutions viscous so that the viscous solutions are not only capable of cleaning, disinfecting, and/or rinsing a contact lens in a lens case but also capable of cleaning and lubricating the contact lens directly in an eye. Such solutions can provide to the user an ability to clean and to rewet lenses anytime anywhere even without taking them out.

19 Claims, No Drawings

LENS CARE SOLUTIONS

This application claims the benefit under 35 U.S.C. § 119 (e) of U.S. provisional application Ser. No. 60/737,206 filed Nov. 16, 2005.

This invention relates generally to aqueous solutions useful for treating contact lenses. Especially, the invention provides solutions containing dexpanthenol in combination with xylitol, preferably further including a viscosity-enhancing agent to make solutions viscous so that the viscous solutions are not only capable of cleaning, disinfecting, and/or rinsing a contact lens in a lens case but also capable of cleaning and lubricating the contact lens directly in an eye. Such solutions can provide to the user an ability to clean and to rewet lenses anytime anywhere even without taking them out.

BACKGROUND OF THE INVENTION

Contact lenses provide a means for vision correction for a wide range of consumers. The advantages of contact lens wear are numerous. Improved convenience and improved appearance in comparison to spectacle glasses are probably the two most important advantages to most consumers. However, contact lenses require stringent care regimes in order to ensure comfort and avoid ocular infections. Proper care of contact lenses typically requires the consumer to periodically clean, disinfect, and/or rinse the lenses. Cleaning usually refers to removal of lipids, proteins or other matter which has become affixed to a lens. Disinfecting usually refers to inactivating of harmful bacteria or fungi whenever the lenses are removed from the eye, which is usually on a daily basis. Rinsing usually refers to removing debris from the lens before placing the lens in the eye.

Traditionally, disinfecting, cleaning and/or rinsing of lenses are not carried out in the eye but occur at the end of day (e.g., in the evening) by immersing a lens in an appropriate lens care solution (for example, a single- or multiple-purpose care solution) in a contact lens case. Such lens cases can be used to store contact lenses between use periods. When it is desired to treat contact lenses, the appropriate contact lens care composition is removed or dispensed from a bottle or container including the composition and passed into the contact lens case in which the contact lenses have been placed. Contact lenses are often left in the lens care solution in the lens case for an extended time, for example, overnight or at least several hours. After treatment, the contact lenses are ready for wear in the eyes of an user. In general, lens care requires the user first taking out of the lenses and then clean, disinfect, and/or rinse them.

But, users may occasionally want to clean and lubricate lenses during the day. Such occasional lens care during the day may be inconvenient for an user since the user needs to take the lenses out of the eyes and then reinsert them into the eyes after cleaning and lubricating.

In addition, a new class of high Dk soft contact lenses, which are made from high oxygen permeable silicone hydrogel materials, have been developed and are commercially available. Such soft contact lenses allow sufficient oxygen to permeate through the lens to the cornea and can have minimal adverse effects on corneal health. This new class of high Dk soft contact lenses can be worn in one of two wearing modalities: daily wear and extended wear (i.e., worn overnight and even continuously over a plurality of days, e.g., up to 30 days). With the advent of extended wear modality, conventional lens care regime and conventional lens care solutions can no longer be used to clean and lubricate lenses while worn in the eye.

It would be desirable to directly clean and lubricate the lenses in the eyes (i.e., without taking out of the lenses from the eyes). Therefore, there exists a need for a lens care solution capable of cleaning and lubricating the contact lens directly in an eye. It is to the provision of a lens care product meeting these and other needs that the present invention is primarily directed.

SUMMARY OF THE INVENTION

In one aspect, the present invention provides a lens care solution comprising dexpanthenol and xylitol.

In another aspect, the present invention provides a new type of lens care solutions that can be used both to treat contact lenses in a lens case and to treat contact lenses while worn in the eye. The lens care solution comprises: dexpanthenol, xylitol, at least one surfactant, a viscosity-enhancing agent in an amount sufficient to provide the solution a viscosity of from about 5 centipoise to about 25 centipoise.

The present invention provides the foregoing and other features, and the advantages of the invention will become further apparent from the following detailed description of the example embodiments set forth herein, read in conjunction with the accompanying figures. The detailed description and figures are merely illustrative of the invention and do not limit the scope of the invention, which is defined by the appended claims and equivalents thereof.

DETAILED DESCRIPTION OF EXAMPLE EMBODIMENTS

The present invention may be understood more readily by reference to the following detailed description of the invention taken in connection with the accompanying drawing figures, which form a part of this disclosure. Unless defined otherwise, all technical and scientific terms used herein have the same meaning as commonly understood by one of ordinary skill in the art to which this invention belongs. Generally, the nomenclature used herein is well known and commonly employed in the art. Conventional methods are used for carrying out the disclosed procedures, such as those provided in the art and various general references. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, reference to singular forms such as "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The invention relates to a lens care composition comprising dexpanthenol and xylitol. A lens care composition of the invention can be used both to treat contact lenses in a lens case and/or to treat contact lenses while worn in the eye.

A lens care composition of the invention can be used to clean contact lenses including hard (PMMA) contact lenses, soft (hydrophilic) contact lenses, and rigid gas permeable (RGP) contact lenses. The soft contact lenses are hydrogel contact lens or silicone hydrogel contact lenses.

A "hydrogel" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

The term "cleaning" means that the solution contains one or more active ingredients in sufficient concentrations to loosen and remove loosely held lens deposits and other contaminants on the surface of the article to be cleaned. While not necessary with the present invention, a user may wish to use the solutions of the present invention in conjunction with digital manipulation (for example, manual rubbing of the lens with a solution) or with an accessory device that agitates the solution in contact with the lens, for example, a mechanical cleaning aid.

In accordance with the invention, a lens care composition is ophthalmic safe. The term "ophthalmically safe" with respect to a lens care solution is meant that a contact lens treated with the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

Dexpanthenol, an alcohol of pantothenic acid, also called Provitamin B5, D-pantothenyl alcohol or D-panthenol, has been used for a long time for healing wounds or in the field of medicinal skin care. It has been found that dexpanthenol can have good cleansing action when present in an amount of at least about 0.2%, preferably at least about 1.0% by weight, more preferably from about 1.1% to about 2.0% by weight in a lens care solution. In addition, dexpanthenol can stabilize the lachrymal film and prevent severe losses of the aqueous layer. Vortex motion of the lachrymal liquid can occur through the insertion of a contact lens, namely because of mechanical eruption or through surface-active substances optionally present in the contact lens solution and can lead to severe loss of the aqueous lachrymal layer. Dexpanthenol can guard against the appearance of dryness, which can lead to a reduced lachrymal film.

Dexpanthenol is used in a preferred contact lens care composition of the invention in an amount of from about 0.2% to about 10% by weight, preferably in an amount of from about 0.5% to about 5% by weight, more preferably in an amount of from about 1% to about 2% by weight, based on the total amount of contact lens care compositions which is advantageously formulated in aqueous solution.

Xylitol is a five-carbon sugar alcohol that is found naturally in many plants and fruits. It has been used as a sweetener in food products such as chewing gum because it is noncaloric and has a sweetness quality equal to that of sugar. To our knowledge, xylitol has not been used in a commercially-available lens care solution. It is found that xylitol can be used as a tonicity agent to adjust the tonicity (osmolality) of a lens care composition. Xylitol is also an excellent humectant agent (i.e., a moisture-retaining agent). The combination of dexpanthenol and xylitol provides a favourable cleansing action and also stabilises the lachrymal film after inserting the contact lenses, whereupon a heavy loss of the aqueous layer is prevented. This guards against the appearance of dryness, which can lead to a reduced lachrymal film. The usage of the active ingredient combination dexpanthenol and xylitol also can substantially improve comfort when wearing contact lenses treated with a lens care solution containing them therein. By adding both dexpanthenol and xylitol in a lens care solution, one can reduce the amount of surfactants used in the solution and thereby reduce any negative effects caused by the surfactants. Also, one may be able to prevent contact lenses from rapidly drying out.

Furthermore, a solution with both dexpanthenol and xylitol shows no cytotoxicity. Addition of dexpanthenol and xylitol in a lens care solution does not have negative effects on the antimicrobial efficacy of the solutions, but it may be able to substantially increase the antimicrobial efficacy of antimicrobial agents present in the contact lens care compositions according to the invention, e.g. of PHMB.

Xylitol is used in a preferred contact lens care composition of the invention in an amount of from about 0.4% to about 10% by weight, more preferably in an amount of from about 1.0% to about 5% by weight, most preferably in an amount of from 1.5% to about 3.5% by weight, based on the total amount of contact lens care composition which is advantageously formulated in aqueous solution.

In accordance with the invention optionally comprise a surfactant for cleaning the contact lens. Combination of a surfactant with dexpanthenol may provide a superior cleaning efficacy to a lens care solution. Any suitable known surfactants can be used in the invention. Examples of suitable surfactants include, but are not limited to poloxamers under the tradename Pluronic from BASF Corp. (Pluronic™ and Pluronic-R™) which are nonionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl) phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); alkyl glucosides and polyglucosides such as products available under the tradename PLANTAREN (Henkel Corp., Hoboken, N.J., USA); and polyethoxylated castor oils commercially available from BASF under the trademark CREMAPHOR.

Preferred surfactants include homopolymers of polyethylene glycol or polyethyleneoxide, and certain poloxamers such as materials commercially available from BASF under the tradenames PLURONIC® 17R4, PLURONIC® F-68NF, PLURONIC® F68LF, and PLURONIC® F127, with PLURONIC® F-68NF (National Formulary grade) being the most preferred. More preferably, a combination of PLURONIC® 17R4 and PLURONIC®F127 is used. When present, poloxamers may be employed at from about 0.001% to about 5% by weight, preferably from about 0.005% to about 1% by weight, more preferably from about 0.05% to about 0.6% by weight.

In a preferred embodiment, the lens care solution of the invention is a multipurpose solution capable of disinfecting, cleaning, and rinsing a contact lens.

The term "disinfecting solution" means a solution containing one or more microbiocidal compounds, that is effective for reducing or substantially eliminating the presence of an array of microorganisms present on a contact lens, which can be tested by challenging a solution or a contact lens after immersion in the solution with specified inoculums of such microorganisms. The term "disinfecting solution" as used herein does not exclude the possibility that the solution may also be useful for a preserving solution or that the disinfecting solution may additionally be useful for daily cleaning, rinsing, and storage of contact lenses.

A solution that is useful for cleaning, chemical disinfection, storing, and rinsing an article, such as a contact lens, is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis.

A disinfecting solution of the invention can be used to disinfect contact lenses against a wide range of microorganisms including but not limited to *Fusarium solani, Staphylococcus aureus, Pseudomonas aeruginosa, Serratia marcescens* and *Candida albicans*. For the purposes of the present invention the term "disinfect" means the rendering non-viable of substantially all pathogenic microbes that are in the vegetative state, including gram negative and gram positive bacteria, as well as fungi. The chemical compounds and compositions that render such pathogenic microbes inactive are known as microbicides.

A disinfecting or MPS solution of the invention must contain a microbicide in a concentration sufficient to effect the desired disinfection of a contact lens. The specific concentrations required for the microbicides useful in this invention must be determined empirically for each microbicide. Some of the factors affecting the effective concentration are specific activity of the microbicide against the specified pathogens, the molecular weight of the microbicide, and the solubility of the microbicide. It is also important that the chosen microbicides be employed in a physiologically tolerable concentration. The list of microbicides which may be employed in the present invention include, but is not in limited to biguanides, biguanide polymers, salts thereof, N-alkyl-2-pyrrolidone, polyquaternium-1, bronopol, benzalkonium chloride, and hydrogen peroxide. The presently useful antimicrobial biguanides include biguanides, biguanide polymers, salts thereof, and mixtures thereof. Preferably, the biguanide is selected from alexidine free-base, salts of alexidine, chlorhexidine free-base, salts of chlorhexidine, hexetidine, hexamethylene biguanides, and their polymers, and salts thereof. Most preferably, the biguanide is a hexamethylene biguanide polymer (PHMB), also referred to as polyaminopropyl biguanide (PAPB).

Typical solutions of this invention contain the microbicides PHMB in an amount of from about 0.01 to about 10 ppm, preferably from about 0.05 to about 5 ppm, more preferably from about 0.1 to about 2 ppm, even more preferably from about 0.2 to about 1.5 pp.

Although PHMB has a broad spectrum of activity and non-specific mode of action against bacteria, PHMB might be able to cause some level of corneal staining (Lyndon Jones, et. al. "Asymptomatic corneal staining associated with the use of balafilcon silicon-hydrogel contact lenses disinfected with a polyaminopropyl biguanide—preserved care regimen", Optometry and Vision Science 79: 753-61(2002)). Therefore, it would be desirable to lower the amount of PHMB in a lens care solution while maintaining the antimicrobial efficacy of the lens care solution.

Where a lens care composition comprises a biguanide or a biguanide polymer (e.g., PHMB) as a microbiocide, it comprises preferably less than 1000 ppm, more preferably less than 500 ppm, even more preferably less than 500 ppm chloride ions. A 0.6% sodium chloride solution, which is probably close to the concentration of sodium chloride in eye, would result in almost 3600 ppm chloride ions in the solution. Such a high concentration of chloride ion would diminish the antimicrobial effectiveness of PHMB, especially those having less than 0.5 ppm PHMB.

The present compositions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. EDTA is low level non-irritating chelating agent and can be synergistic with PHMB to increase antimicrobial efficacy. Typical amount of EDTA is from about 0.001% to about 1% by weight, preferably from about 0.002% to about 0.5% by weight, more preferably from about 0.004% to about 0.1, even more preferably from about 0.005 to about 0.05, based on the total amount of contact lens care composition.

The composition of the present invention preferably contains a buffering agent. The buffering agents maintain the pH preferably in the desired range, for example, in a physiologically acceptable range of about 6.5 to about 7.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (trometamol, 2-amino-2-hydroxymethyl-1,3-propanediol), bis-aminopolyols, phosphate buffers, e.g. $Na_2HPO_4$, $NaH_2PO_4$, and $KH_2PO_4$ or mixtures thereof. The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The preferred buffering agents are bis-aminopolyols of formula (I)

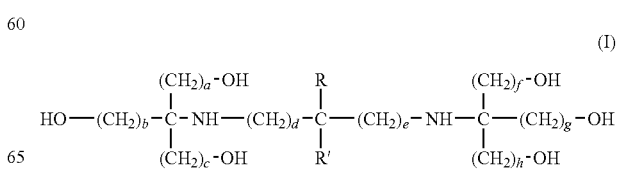

(I)

wherein a, b, c, d, e, f, g, and h are independently an integer from 1 to 6; and R and R' are independently selected from the group consisting of —H, —CH$_3$, —(CH$_2$)$_{2-6}$—H, and —(CH$_2$)$_{1-6}$—OH. In the present invention, the buffering agents described by formula (I) may be provided in the form of various water-soluble salts. A most preferred bis-aminopolyol is 1,3-bis(tris[hydroxymethyl]methylamino)propane (bis-TRIS-propane).

It has been found that bis-TRIS-propane can exhibit a synergy with certain microbicides (e.g., PHMB) and fungicides, resulting in a microcidal activity significantly higher than the activity of these same active ingredients used in conjunction with other buffers. BIS-TRIS propane is described under biological buffers in Biochemicals and Reagents, Sigma-Aldrich Co., 2000-2001 edition. The specific structure of bis-TRIS-propane is shown in formula II.

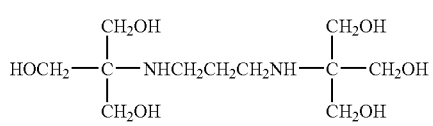

The dissociation constants for this dibasic compound are pKa$_1$=6.8 and pKa$_2$=9.5 which renders aqueous solutions of this compound useful as a buffering agent in a broad pH range from about 6.3 to 9.3. bis-TRIS-propane at a concentrations used in this invention is harmless to the eye and to known contact lens materials and is, therefore, ophthalmically compatible.

Preferably, the solutions of the present invention have a low concentration of phosphate ions, preferably substantially free of phosphate ions. Solutions having less than a total of 1500 ppm of phosphate ion and chloride ion have been surprisingly discovered to be effective against a broad spectrum of microorganisms, including C. albicans. Previously known solutions generally had very high concentrations of both phosphate ions and chloride ions, due to their use large amounts of phosphate buffers, sodium or potassium chloride tonicity agents, and hydrochloric or phosphoric acid to adjust pH downward.

A lens care composition of the invention preferably comprises a lubricant. "Lubricants" as used herein refer to any compounds or materials which can enhance surface wettability of a contact lens and/or the eye or reduce the frictional character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methaacrylamide, a copolymer of acrylamide or methacrylamide with one or more hydrophilic vinylic monomers, mixtures thereof.

In a preferred embodiment, the lens care solution is a thickened lens care solution having a suitable viscosity for in-eye cleaning and lubrication of lenses. Preferably, the lens care solution is a multiple-purpose solution free of hydrogen peroxide.

The thickened lens care solution should have a viscosity sufficient low to enable it to be controllably dispensed from a solution container when subjected to applied hand and/or finger pressure to the container by an user, yet has a viscosity sufficiently large to prolong its staying time in the eye long enough for in-eye cleaning and lubrication of lenses. The thickened lens care solution has a viscosity of preferably from about 5 centipoise to about 25 centipoise, more preferably from about 10 centipoise to about 20 centipoise.

The solution may also contain one or more viscosity-enhancing agents. The viscosity-enhancing components preferably are effective at low or reduced concentrations, are compatible with the other components of the present solutions and are nonionic. Such viscosity-enhancing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity-enhancing component may also act to cushion the impact on the eye surface during insertion and serves also to alleviate eye irritation.

Suitable viscosity-enhancing components include, but are not limited to, polyvinylpyrrolidone, water soluble natural gums, cellulose-derived polymers, and the like. Useful natural gums include guar gum, gum tragacanth and the like. Examples of useful cellulose-derived polymers as viscosity-enhancing agents include without limitation cellulose ethers.

Exemplary preferred cellulose ethers are methyl cellulose (MC), ethyl cellulose, hydroxymethylcellulose, hydroxyethyl cellulose (HEC), hydroxypropylcellulose, hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of from about 0.01% to about 5% by weight, preferably from about 0.05% to about 3% by weight, even more preferably from about 0.1% to about 1% by weight, based on the total amount of contact lens care composition. It is believed that a cellulose ether can be used to increase the viscosity of a lens care and also can serve as a lubricant in the lens care composition.

A very useful viscosity-enhancing component is polyvinylpyrrolidone (PVP). The polyvinylpyrrolidone (PVP) used in the compositions of the invention is a linear homopolymer or essentially a linear homopolymer comprising at least 90% repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrolidinone, and 1-ethenyl-2-pyrolionone (CAS registry number 9003-39-8). The PVP used in the present invention suitably has a weight average molecular weight of about 10,000 to 250,000, preferably 30,000 to 100,000. Such materials are sold by various companies, including ISP Technologies, Inc. under the trademark PLASDONE™ K-29/32, from BASF under the trademark KOLLIDON™ for USP grade PVP, for example KOLLIDON™ K-30 or K-90. While the invention is not limited to any specific PVP, K-90 PVP is preferred, more preferably pharmaceutical grade.

The contact lens care solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout, provided that the contact lenses to be treated are not damaged.

The isotonicity with the lachrymal fluid, or even another desired tonicity, may be adjusted by adding xylitol and optionally organic or inorganic substances which affect the tonicity. Suitable occularly acceptable tonicity agents include, but are not limited to sodium chloride, potassium chloride, glycerol, propylene glycol, polyols, mannitols, sorbitol, and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

The contact lens care compositions according to the invention are produced in known manner, in particular by means of conventional mixing of the constituents with water or dissolving the constituents in water.

Aqueous solutions comprising the following components have been found to be particularly useful in cleaning and disinfecting contact lenses:

| | |
|---|---|
| Dexpanthenol | 0.5% to 5% |
| Xylitol | 1% to 5% |
| Bis-TRIS-propane | 0.001% to 2% |
| poloxamer | 0.005% to 1% |
| PHMB | less than 2.0 ppm |
| EDTA | less than 0.3% |
| Cellulose ether | 0.05% to 3% |
| Chloride ions | less than 1000 ppm |

Even more preferred are those solutions having the following components:

| | |
|---|---|
| dexpanthenol | 1% to 2% |
| Xylitol | 1.5% to 3.5% |
| Bis-TRIS-propane | 0.05% to about 0.30% |
| poloxamer | 0.05% to 0.6% |
| PHMB | less than 1.5 ppm |
| EDTA | 0.01% to 0.2% |
| Cellulose ether | 0.1% to 1% |
| Chloride ions | less than 500 ppm |

The contact lens care compositions according to the invention are suitable for all kinds of contact lenses. This includes in particular the so-called hard and soft contact lenses, and also the so-called hard-flexible or highly gas-permeable contact lenses. The contact lens care compositions according to the invention have cleaning action and, in addition, optionally have antimicrobial action.

The compositions according to the invention are especially suitable for cleaning and, where appropriate, for disinfecting contact lenses. The contact lens care compositions according to the invention are used in known manner, e.g. by bringing the contact lens into contact with the contact lens care composition for a period of time that is sufficient to clean or disinfect it. Depending on the lens type and the degree of soiling, a sufficient time span ranges from a few minutes to about 24 hours, preferably from about 1 to about 12 hours, more preferably from about 2 to about 8 hours, even more preferably from about 4 to about 12 hours, has proved to be practicable.

The contacting temperature is in the range preferred from about 0° C. to about 100° C., more preferably from about 10° C. to about 60° C., still more preferably from about 15° C. to about 37° C. Contacting at or about ambient temperature is very convenient and useful. The contacting preferably occurs at or about atmospheric pressure.

Where a lens care solution is a multipurpose solution, the contacting preferably occurs for a time in the range of from about 5 minutes or about 1 hour to about 12 hours or more. Especially preferred are those solutions have 0.5 ppm or less PHMB and can obtain at least a 1 log reduction in *C. albicans* within 15 minutes of contact with the lens. Also preferred are those having less than 0.25 ppm PHMB and obtaining at least 1.0, more preferably 1.5 log, reduction in *C. albicans* within 15 minutes, more preferably at least a 2.0 log reduction in *C. albicans* within 30 minutes.

The contact lens can be contacted with the solution by immersing the lens in the solution. Although not necessary, the solution containing the contact lens can be agitated, for example, by shaking the container containing the solution and contact lens, to at least facilitate removal of deposit material from the lens.

The contact lens can be contacted with the solution of the invention while it is still worn on an eye. The solution of the invention can be applied directly into eye to clean and lubricate a contact lens worn on the eye.

In another aspect, the invention provides a method for cleaning and/or disinfecting a contact lens. The method comprises the step of bringing one or more contact lenses into contact with the contact lens care composition of the invention for a period of time that is sufficient to clean and/or disinfect the one or more contact lenses.

The solutions and methods of the present invention may be used in conjunction with enzymes to remove debris or deposit material from the contact lens as the solutions of the present invention have no negative effect on the proteolytic activity of enzymes, such as UNIZYME®. After such contacting step, the contact lens optionally may be manually rubbed with saline, or even rinsed without rubbing, to remove further deposit material from the lens. The cleaning method can also include rinsing the lens substantially free of the liquid aqueous medium prior to returning the lens to a wearer's eye.

In a further aspect, the invention provides a method for cleaning and lubricating a contact lens while it is still worn on an eye, comprises the step of dispensing a desired amount of a lens care solution of the invention directly into the eye wearing the contact lens.

In another further aspect, the invention provides a kit for cleaning and/or disinfecting a contact lens. The kit comprises a bottle containing a lens care solution, wherein the lens care solution can be dispensed from the bottle into a container where the lens care solution is in contact with the contact lens for a period of time sufficient long to clean and/or disinfect them. The lens care solution comprises dexpanthenol and xylitol.

The kit can optionally include one or more lens care cases for treating contact lenses and/or instructions for how to use the lens care solution to clean and/or disinfect contact lenses.

In a still further aspect, the invention provides a kit for cleaning and lubricating a contact lens directly in an eye. The kit comprises a bottle containing a lens care solution, wherein the lens care solution can be applied directly into an eye wearing the contact lens, wherein the lens care solution comprises dexpanthenol, xylitol and a viscosity-enhancing agent in an amount sufficient to provide the lens care solution a viscosity of from about 5 centipoises to about 25 centipoises.

The kit can optionally include instructions for how to use the lens care solution to clean and lubricate contact lenses directly in eyes.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Furthermore, titles, headings, or the like are provided to enhance the reader's comprehension of this document, and should not be read as limiting the scope of the present invention. Accordingly, the spirit and scope of the appended claims should not be limited to the description of the preferred versions contained therein.

What is claimed is:

1. An aqueous lens care solution, comprising dexpanthenol, xylitol and a mucin-like material, wherein the mucin-like material is selected from the group consisting of polyglycolic acid and polylactides, wherein the amount of xylitol is from 0.4% to about 10% by weight.

2. The solution of claim 1, wherein the amount of dexpanthenol in the solution is from about 0.2% to about 10% by weight.

3. The solution of claim 1, wherein the amount of dexpanthenol in the solution is from about 0.5% to about 5% by weight.

4. The solution of claim 2, further comprising one or more ingredients selected from the group consisting of a buffering agent, a surfactant, a lubricant, a viscosity-enhancing agent, a complexing agents, an antimicrobial agent, and a mixture thereof.

5. The solution of claim 4, wherein the solution comprises a buffering agent of formula (I)

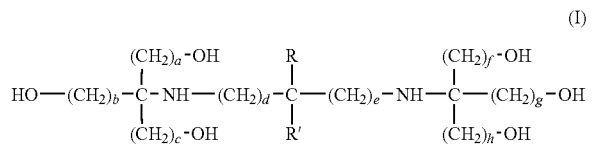

(I)

wherein a, b, c, d, e, f, g, and h are independently an integer from 1 to 6; and R and R' are independently selected from the group consisting of —H, —CH$_3$, —(CH$_2$)$_{2-6}$—H, and —(OH$_2$)$_{1-6}$—OH.

6. The solution of claim 5, wherein the buffering agent is 1,3-bis(tris[hydroxymethyl]methyl-amino)propane.

7. The solution of claim 4, wherein the solution comprises a biguanide or a biguanide polymer.

8. The solution of claim 7, wherein the biguanide or biguanide polymer is a hexamethylene biguanide polymer (PHMB).

9. The solution of claim 8, further comprising ethylenediaminetetraacetic acid (EDTA) and/or salts thereof.

10. A multipurpose contact lens solution which is an aqueous solution, comprising:
    (a) from about 0.5% to about 5% by weight of dexpanthenol;
    (b) from about 1% to about 3.5% by weight of xylitol;
    (c) from about 0.05% to 3% of a viscosity-enhancing agent;
    (d) from about 0.001% to about 2% by weight of 1,3-bis(tris[hydroxymethyl]methyl-amino)propane
    (e) less than about 2 ppm hexamethylene biguanide polymer
    (f) from 0.005% to about 1% by weight of a non-ionic surfactant
    (g) less than about 0.3% by weight of EDTA;
    (h) less than 1000 ppm chloride ions, and
    (i) a-mucin-like material,
wherein the solution has a tonicity of 200 to 450 mOsm/kg and a pH of between 6 and 8, wherein the mucin-like material is selected from the group consisting of polyglycolic acid and polylactides.

11. The solution of claim 10, wherein the viscosity-enhancing agent is present in the solution in an amount sufficient to provide the solution a viscosity of from about 5 centipoises to about 25 centipoises.

12. The solution of claim 11, wherein the viscosity-enhancing agent comprises a cellulose ether, a polyvinyl alcohol, a polyvinylpyrrolidone, or a mixture thereof.

13. The solution of claim 11, wherein the viscosity-enhancing agent is methyl cellulose (MC), ethyl cellulose, hydroxymethylcellulose, hydroxyethyl cellulose (HEC), hydroxypropylcellulose, hydroxypropylmethyl cellulose (HPMC), or a mixture thereof. More preferably, a cellulose ether is hydroxyethyl cellulose (HEC), hydroxypropylmethyl cellulose (HPMC), or a mixture thereof.

14. The solution of claim 11, wherein the non-ionic surfactant comprises a nonionic surfactant consisting of block copolymers of propylene oxide and ethylene oxide.

15. A multipurpose contact lens solution which is an aqueous solution, comprising:
    (a) from about 1% to about 2% by weight of dexpanthenol;
    (b) from about 1.5% to about 3.5% by weight of xylitol;
    (c) a cellulose ether in an amount sufficient to provide the solution a viscosity of from about 5 centipoises to about 25 centipoises;
    (d) from about 0.05% to about 0.30% by weight of 1,3-bis(tris[hydroxymethyl]methyl-amino)propane;
    (e) less than about 1.5ppm hexamethylene biguanide polmer;
    (f) from about 0.05% to about 0.6% by weight of one or more nonionic surfactants consisting of block copolymers of propylene oxide and ethylene oxide;
    (g) less than about 0.2% by weight of EDTA;
    (h) less than 1000 ppm chloride ions, and
    (i) a-mucin-like material,
wherein the solution has a tonicity of 200 to 450 mOsm/kg and a pH of between 6 and 8, wherein the mucin-like material is selected from the group consisting of polyglycolic acid and polylactides.

16. The solution of claim 15, wherein the solution comprises from about 0.5 ppm to about 1.2 ppm hexamethylene biguanide polmer.

17. The solution of claim 15, wherein the solution comprises less than about 0.25% by weight of one or more nonionic surfactants consisting of block copolymers of propylene oxide and ethylene oxide.

18. A kit for cleaning and/or disinfecting a contact lens, comprising a bottle containing a lens care solution, wherein the lens care solution can be dispensed from the bottle into a container where the lens care solution is in contact with the contact lens for a period of time sufficient long to clean and/or disinfect them, wherein the lens care solution comprises dexpanthenol, a-mucin-like material and xylitol, wherein the mucin-like material is selected from the group consisting of polyglycolic acid and polylactides.

19. A kit for cleaning and lubricating a contact lens directly in an eye, comprising a bottle containing a lens care solution, wherein the lens care solution can be applied directly into the eye wearing the contact lens, wherein the lens care solution comprises dexpanthenol, a-mucin-like material, xylitol and a viscosity-enhancing agent in an amount sufficient to provide the lens care solution a viscosity of from about 5 centipoises to about 25 centipoises, wherein the mucin-like material is selected from the group consisting of polyglycolic acid and polylactides.

* * * * *